United States Patent
Garcia et al.

(10) Patent No.: US 8,088,772 B2
(45) Date of Patent: Jan. 3, 2012

(54) SULFONAMIDES AND THEIR USE AS A MEDICAMENT

(75) Inventors: Gabriel Garcia, Lansdale, PA (US); Pierre Daram, Uetikon am See (CH); Barbara Froesch, Mettmenstetten (CH); Frank Jaschinski, Obertraubling (DE); Guy Lemaillet, Meilen (CH); Cornelia Marty-Ernst, Binz (CH); Elena Marzi, München (DE); Leonardo Scapozza, Grens (CH)

(73) Assignee: The Genetics Company, Inc., Schlieren (CH)

( * ) Notice: Subject to any disclaimer, the term of this patent is extended or adjusted under 35 U.S.C. 154(b) by 0 days.

(21) Appl. No.: 12/517,691

(22) PCT Filed: Dec. 11, 2007

(86) PCT No.: PCT/EP2007/010830
§ 371 (c)(1),
(2), (4) Date: May 26, 2010

(87) PCT Pub. No.: WO2008/071398
PCT Pub. Date: Jun. 19, 2008

(65) Prior Publication Data
US 2010/0249135 A1     Sep. 30, 2010

(30) Foreign Application Priority Data
Dec. 11, 2006   (EP) ..................................... 06025619

(51) Int. Cl.
| | |
|---|---|
| A61K 31/5375 | (2006.01) |
| A61K 31/44 | (2006.01) |
| A61K 31/415 | (2006.01) |
| A61K 31/18 | (2006.01) |
| C07D 295/00 | (2006.01) |
| C07D 231/10 | (2006.01) |
| C07D 213/00 | (2006.01) |
| C07D 309/00 | (2006.01) |

(52) U.S. Cl. .................... 514/239.5; 514/347; 514/357; 514/406; 514/603; 544/160; 546/293; 546/332; 548/377.1; 564/81

(58) Field of Classification Search ............... 514/239.5, 514/347, 357, 406, 603; 544/160; 546/293, 546/332; 548/377.1; 564/81
See application file for complete search history.

(56) References Cited

FOREIGN PATENT DOCUMENTS
| | | | | |
|---|---|---|---|---|
| WO | WO 03/006447 | | 1/2003 | |
| WO | WO 2004/080972 | * | 9/2004 | ................. 548/356.1 |

OTHER PUBLICATIONS

Giannotti, Danilo. New Dibenzothiadiazepine Derivatives with Antidepressant Activities. J. Med. Chem. 1991, 34, 135601362.*
Document No. XP002436957; Database Chemcats, Feb. 15, 2007, Ambinter, 50 Avenue de Versailles, Paris, France 75016. Chemical Abstracts Service, Columbus, Ohio, USA.
Document No. XP002436956; Database Chemcats, Mar. 6, 2007, Anamine, 23 Alexandra Motrosova Street, Kiev, Ukraine, 01103, Chemical Abstracts Service, Columbus, Ohio USA.

* cited by examiner

*Primary Examiner* — Rebecca Anderson
*Assistant Examiner* — Samantha Shterengarts
(74) *Attorney, Agent, or Firm* — RatnerPrestia

(57) ABSTRACT

The present invention relates to the use of a sulfonamide compound of formula (I): wherein $R_1$ is selected from the group consisting of H, CN, halogen, trifluoromethyl, methyl, ethyl, hydroxy, methoxy, ethoxy, morpholino, $R_2$ is selected from H, phenyl, substituted phenyl, CN, —$SO_2R$, wherein R is phenyl or morpholino, —NC(O)Me, —NC(O)Et, —$CH_2$C(O)OMe, $CH_2$C(O)OEt, $R_3$ is selected from the group consisting of H, $NO_2$, $NH_2$, halogen, —COOMe, —COOEt, RC(O)N—, morpholino, $R_4$ is selected from the group consisting of H, a branched or unbranched methyl, ethyl, propyl, butyl, pentyl, methoxy, ethoxy, propoxy, butoxy, a substituted or unsubstituted phenyl, alkinyl, $Me_2SO_2$—, COOR, wherein R is a branched or unbranched methyl, ethyl, propyl, butyl, pentyl, -MeOC(O)—, a substituted or unsubstituted five or sixmembered aromatic or non-aromatic heterocyclic system with one, two or three heteroatoms, a hetaryl system, a condensed benzoheterocyclic system, X is a linker comprising 2 or 3 atoms, selected from the group consisting of —NH—NH—, —NH—NH—CH2—, ethinyl, —NH—C(O)—$CH_2$—, —NH—NH—$SO_2$—, —C(O)—NH—$CH_2$—, —NH—N=CH—, —NH—N=C(Me)-, a —NH—N=CH— motif being part of a heterocyclic system, preferably a substituted or unsubstituted pyrazole or pyridazine system, and pharmaceutically active salts thereof. Further, the invention relates to the use of these compounds as a medicament, especially for the treatment of cancer.

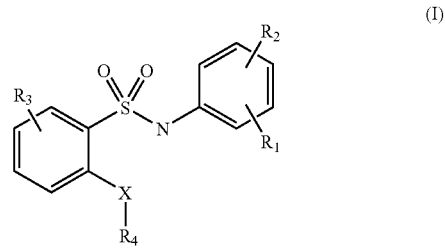

(I)

24 Claims, No Drawings

SULFONAMIDES AND THEIR USE AS A MEDICAMENT

This is a U.S. National Phase application of application number PCT/EP2007/010830, filed Dec. 11, 2007 (which is incorporated herein by reference in its entirety), which claims priority benefit of EP 06025619.5 (filed Dec. 11, 2006).

The present invention relates to sulfonamide compounds that inhibit the interaction between β-catenin and BCL9 and/or BCL9L proteins, i.e. compounds which inhibit the Wnt transduction pathway. Further the present invention relates to the use of these compounds for the preparation of a pharmaceutical composition which is useful in the treatment of cancer.

Inhibitors as contemplated in the present invention can be used for stem cell research or for the treatment of diseases characterized by aberrant Wnt activation such as cancer, bone and cartilage diseases {M., 2005 #198} {Westendorf J J, 2004 #199}. For instance, pathological activation of the Wnt pathway has been extensively reported for colorectal cancer (reviewed in {Pinto D, 2005 #197}, hepatocellular carcinoma {Lee H C, 2006 #194}, breast cancer {Howe L R, 2004 #196}, melanomas {Larue L, 2006 #195}, mesotheliomas (reviewed in {Fox S., 2006 #191}), lymphomas {Bellei B, 2004 #193} and leukemias {Jamieson C H, 2004 #192}. Furthermore, since the Wnt pathway also plays a fundamental role in T-cell development (Staal, Meeldijk et al. 2001; Staal and Clevers 2003), the Wnt signal transduction pathway inhibitors disclosed herein might also be used as immunosuppressant drugs, e.g. after organ transplantation or to treat certain autoimmune diseases such as Lupus erythematosus, multiple sclerosis and rheumatoid arthritis {M., 2005 #198}.

Wnt/Wg proteins exert many of their effects on vertebrate animal development by activating the expression of specific target genes in responding cells. Several of these target genes have been identified and some of their functions are consistent with control of cellular growth, differentiation, and survival (He, Sparks et al. 1998; Crawford, Fingleton et al. 1999; Tetsu and McCormick 1999; Kolligs, Nieman et al. 2002; Shtutman, Zhurinsky et al. 2002).

An intricate machinery has been identified which normally marks β-catenin for degradation by phosphorylation. Importantly, the tumor suppressors APC and Axin are essential components of this β-catenin destruction complex. Upon activation of the Wnt pathway, β-catenin escapes this phosphorylation reaction, accumulates in the cytoplasm, and enters the nucleus, where it associates with TCF proteins and the recently identified Lgs/BCL9 {Kramps, 2002 #167} proteins to function as a transcriptional coactivator of target genes.

This set-up, in which the key transducer is continuously held in check, is highly susceptible to mutations in its inhibitory components. In fact, mutations in the downstream components of Wnt signalling have been found to be associated with a variety of human cancers (Kinzler and Vogelstein 1996; Miller, Hocking et al. 1999). For example, germline APC mutations can cause hundreds of benign colorectal tumors, some of which develop into cancer. Somatic mutations of the APC gene are associated with 85% of sporadic colorectal adenomas and carcinomas (Kinzler and Vogelstein 1996), mutations in the phosphorylation sites of β-catenin have been found in many human cancers, such as colorectal cancer, hepatocellular carcinoma, and melanoma (Morin, Sparks et al. 1997; Rubinfeld, Robbins et al. 1997) (Caca, Kolligs et al. 1999), and axin mutations have been identified in hepatocellular carcinoma (Satoh, Daigo et al. 2000). Moreover, several mutations and/or changes in expression of upstream components like LRP5, sfrps, WIF-1, DKK or Wnt ligands have not only been linked to cancer, but also to bone and cartilage diseases {Westendorf, 2004 #199}, {Sen, 2005 #198} {Moon, 2004 #216}. Since all these mutations lead to the accumulation of nuclear β-catenin, this protein and its interacting partners has emerged as attractive targets to inhibit Wnt dependent gene expression.

In fact, inhibitors of the Wnt pathway that target the β-Catenin-Tcf4 interaction and processes for finding such inhibitors have been disclosed:

This topic has also been the subject of several patent applications: International patent application WO 98/42296 discloses purified proteins and conventional processes for screening for inhibitors. International patent application WO 02/44378 describes a conventional process for screening for Tcf-β-Catenin inhibitors. International patent application WO 03/006447 relates to Tcf4-β-Catenin inhibitors. International patent application WO 02/096430 discloses cephalosporine derivatives as small molecule β-catenin inhibitors.

International patent application WO 01/19353A2 characterizes a "targetable" pocket in β-Catenin using a 3D-model of the Tcf4-β-Catenin interaction. It also describes in silico screening processes based on said interaction for identifying inhibitors as well as a number of inhibitors identified by this process.

The main disadvantage of the above mentioned approach is the nature of the β-Catenin-Tcf4 interaction. In particular, this protein-protein interaction surface is quite large and it is at least partially shared with other β-Catenin interacting partners like ECadherin and APC (Graham, Weaver et al. 2000; Eklof Spink, Fridman et al. 2001; Huber and Weis 2001; Poy, Lepourcelet et al. 2001), which raises serious questions about its specificity. In this context, alternative targets for the Wnt pathway are needed.

The Legless (Lgs)/BCL9 family of proteins was identified in a genetic screening for novel positive regulators of the Wnt pathway downstream of the APC tumor supressor in *Drosophila melanogaster*. In human there are two homologues, BCL9 and BCL9-like (BCL9L, also known as B9L or BCL9-2), which, like the *Drosophila* protein, act as essential adaptor molecules between the transcriptional active components Pygo and β-Catenin {Kramps, 2002 #167} {Katoh, 2005 #211}. Binding of BCL9 proteins to β-Catenin is essential for the propagation of the Wnt signaling in cancer cells {Adachi S, 2004 #200} {Brembeck F H, 2004 #201}. Competitor peptides that are capable of disrupting this protein-protein interaction or reduction of BCL9L expression by small interfering RNAs (siRNA) strongly inhibit the Wnt pathway and lead to differentiation of cancer cells from a non-differentiated malignant type into moderately to well differentiated tissue ({Brembeck F H, 2004 #201} {Adachi S, 2004 #200}, US2002/0086986). However, despite their specific and potent inhibitory activity on the Wnt pathway these peptides or siRNA molecules do not represent ideal drugs for tumor therapy because of the poor membrane permeability and poor systemic availability.

Therefore on of the objects of the present invention was to provide novel inhibitors of the beta-Catenin/BCL9-BCL9L interaction, in particular those compounds that have improved drug features, such as lower molecular weight and ideally good cellular permeability.

This object is solved by providing novel sulfonamide compounds of formula I:

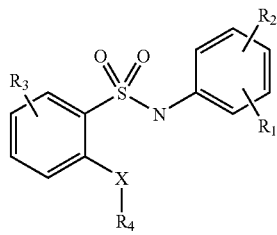

wherein

R₁ is selected from the group consisting of H, CN, halogen, trifluoromethyl, methyl, ethyl, hydroxy, methoxy, ethoxy, morpholino, R₂ is selected from H, phenyl, substituted phenyl, CN, —SO₂R, wherein R is phenyl or morpholino, —NC(O)Me, —NC(O)Et, —CH₂C(O)OMe, CH₂C(O)OEt, R₃ is selected from the group consisting of H, NO₂, NH₂, halogen, —COOMe, —COOEt, RC(O)N—, morpholino, R₄ is selected from the group consisting of H, a branched or unbranched methyl, ethyl, propyl, butyl, pentyl, methoxy, ethoxy, propoxy, butoxy, a substituted or unsubstituted phenyl, alkinyl, Me₂SO₂—, COOR, wherein R is a branched or unbranched methyl, ethyl, propyl, butyl, pentyl, -MeOC(O)—, a substituted or unsubstituted five or sixmembered aromatic or non-aromatic heterocyclic system with one, two or three heteroatoms, a hetaryl system, a condensed benzo-heterocyclic system, preferably a substituted or unsubstituted phenyl, pyridinyl, naphthyl, quinolinyl, isoquinolinyl, isoxazolinyl, thiophenyl, 1,3,4-thiadiazazolidinyl, furanyl, tetrahydroquinolinyl, tetrahydroisoquinolinyl, furanyl, and chromen-2-only, X is a linker comprising 2 or 3 atoms, selected from the group consisting of —NH—NH—, —NH—NH—CH₂—, ethinyl, —NH—C(O)—CH₂—, —NH—NH—SO₂—, —C(O)—NH—CH₂—, —NH—N=CH—, —NH—N=C(Me)-, a —NH—N=CH— motif being part of a heterocyclic system, preferably a substituted or unsubstituted pyrazole or pyridazine system or of a imidazolyl, imidazolidin-2-onyl, triazolyl and tetrazolyl system, and pharmaceutically active salts thereof.

In preferred embodiments of the invention R₁ is located in ortho position and these compounds are represented by formula Ia. The ortho position is the 2 position of the ring linked to the N atom of the sulphonamide moiety. The meanings of the substituents are as above:

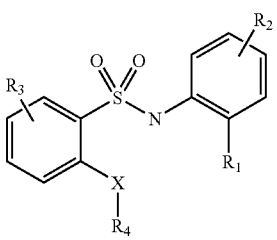

In preferred embodiments, R₁ is a halogen. In the context of the present invention, "halogen" means Cl, Br, I and F. Especially preferred are Cl, Br and F.

In a still further preferred embodiment, R₂ is located in meta position. For a better understanding, the meta position is the 3 or 5 position of the ring linked to the N atom of the sulphonamide moiety. Most preferred is in this context the 5 position, i.e R₁ and R₂ are in para position to one another and these compounds are represented by formula Ib. The meanings of the substituents are as above

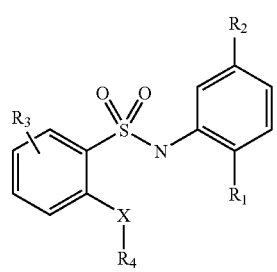

In other preferred embodiments, R₂ is located on para position, i.e in the 4 position position of the ring linked to the N atom of the sulphonamide moiety.

In further preferred embodiments of the invention R₃ is located in ortho position and X is H. The ortho position is the 2 position of the ring linked to the sulphur atom, of the sulphonamide moiety. In these cases, R₃ is halogen, most preferred are Cl and Br. The preferred structural motifs can be represented by the following formulae Ic and Id:

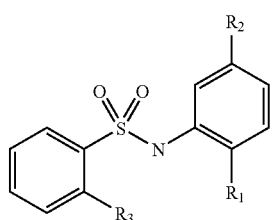

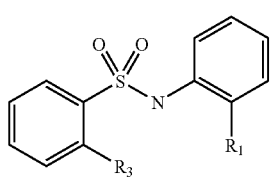

In these preferred embodiments according to formulae Ic and Id, X is H.

In still further preferred embodiments, R₃ is located in meta position according to formula Ie. The meta position is the 5 position of the ring linked to the sulphur atom, of the sulphonamide moiety.

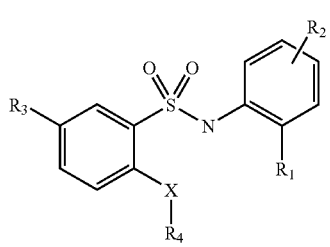

Especially preferred structural motifs are represented by formulae If, Ig and Ih (The meanings of the substituents are as above

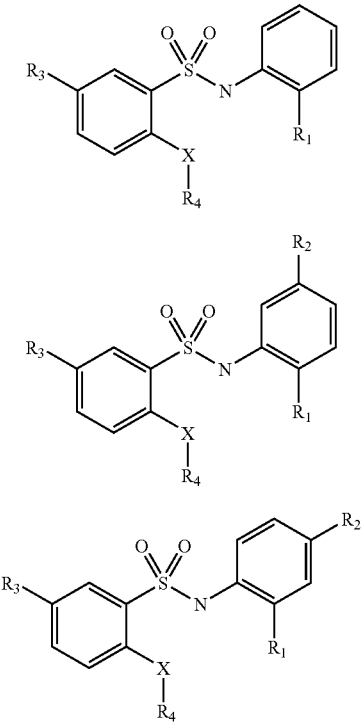

As can be seen it is especially preferred that the X—R$_4$ group is located in ortho position and is in para position to R$_3$.

In these formulae it is especially preferred that R$_3$ is H, halogen, NO$_2$, NH$_2$ or an acidamide (—C(O)NR'$_2$ wherein R' is H, methyl, ethyl or n- and i-propyl) rest.

X is preferably selected from the group consisting of —NH—NH—, —NH—NH—CH$_2$—, ethinyl (—CC—R", wherein R" is H a C$_1$ to C$_8$ branched or unbranched, substituted or unsubstituted alkyl rest, preferably methyl, ethyl, n- and i-propyl, n-, i- and t-butyl, pentyl, n-pentyl, n-hexyl, cylohexyl, n-heptyl and n-octyl or cyano substituted derivatives thereof), —NH—C(O)—CH$_2$—, —NH—NH—SO$_2$—, —C(O)—NH—CH$_2$—, —NH—N=CH—, —NH—N=C(Me)-, and a —NH—N=CH— motif being part of a substituted or unsubstituted pyrazole system.

It is especially preferred that R$_4$ is selected from the group consisting of a branched or unbranched methyl, ethyl, propyl, butyl, pentyl, methoxy, ethoxy, a substituted or unsubstituted phenyl, a substituted alkinyl, Me$_2$SO$_2$—, COOR, wherein R is a branched or unbranched methyl, ethyl, propyl, butyl, pentyl, -MeOC(O)—, a substituted or unsubstituted pyrazolyl or pyridinyl, a hetaryl system, a condensed benzoheterocyclic system.

In most preferred embodiments of the inventions, R$_3$ is NO$_2$.

In further especially preferred embodiments of the present invention, X is a structural motif comprising 2 nitrogen atoms, more preferably selected from the group consisting of —NH$_2$—NH—CH$_2$—, —NH$_2$—NH$_2$—SO$_2$—, —NH—N=CH$_2$—, a —NH—N=CH— motif being part of a substituted or unsubstituted pyrazole system, —NH$_2$—NH—C(O)—.

Especially preferred specific compounds which exhibit especially high activities in cellular assays are represented by the following formulae:

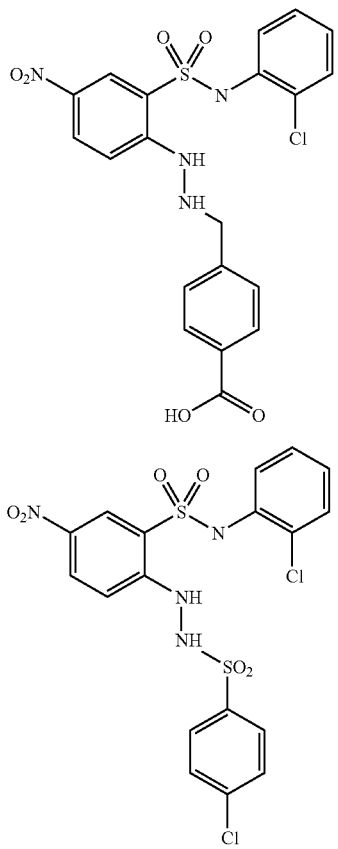

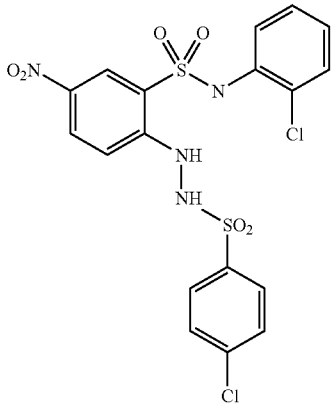

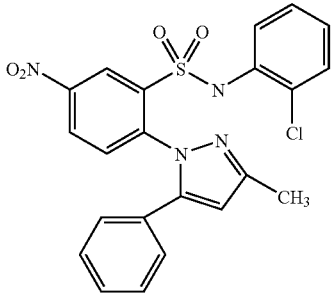

Still further preferred compounds with high activities are the compounds with formulae V

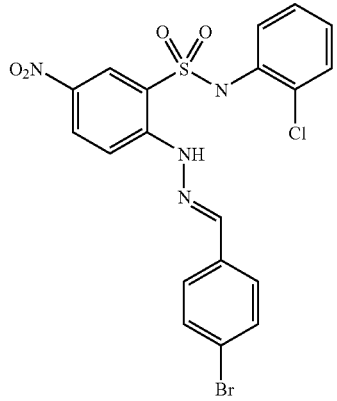

-continued

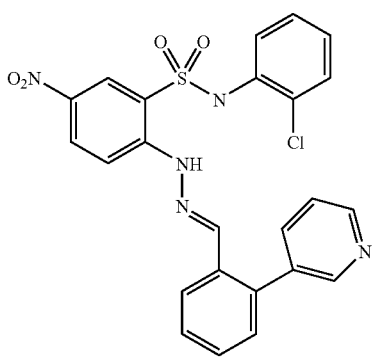

(VI)

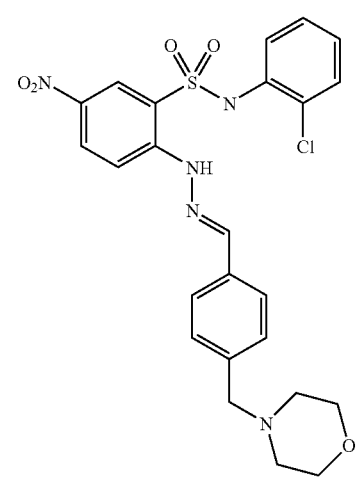

(VII)

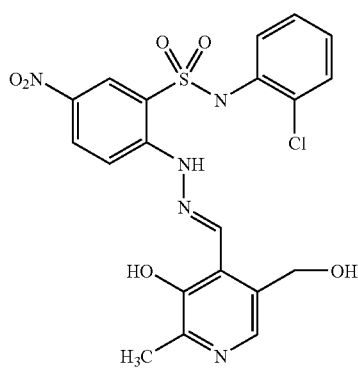

(VIII)

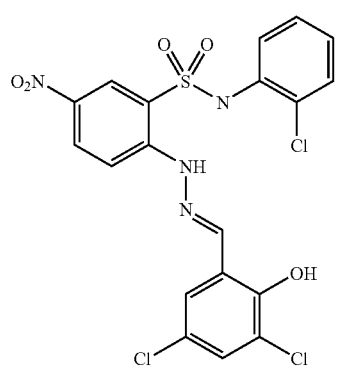

(IX)

A still further object of the invention is the use of a compound according to the invention as a medicament and for the manufacture of a pharmaceutical composition for the treatment of cancer (können Sie schon sagen welche KREB-SARTEN DAS SEIN KÖNNTEN? Bei den Igs Anmeldungen hatten wir zumeist colon caner).

The invention relates further to a pharmaceutical composition comprising a compound according the invention or a pharmaceutically acceptable salt thereof and in still further embodiments further comprising at least one pharmaceutically acceptable carrier, diluent or excipient.

Table 1 shows In vitro activities of compounds according to the invention. TGC ID refers to the applicants internal identification number; Specificity values depict compound's specificity for inhibition of the βCatenin-BCL9 (specific means that they do not significantly inhibit E-Cadherin-βCatenin, Tcf-4-βCatenin or BCL9-Pygo interactions); MW means molecular weight.

The compounds according to the invention may be administered alone or in the form of a pharmaceutically acceptable salt thereof. A pharmaceutical composition comprising a compound according to the invention or a pharmaceutically active salt thereof may further comprise at least one pharmaceutically acceptable carrier, diluent or excipient. It is understood that in specific embodiments also further active compounds are contained within the composition.

The compounds according to the invention may be formulated for topical, oral, transdermal, parenteral, sublingual, intranasal, intrathecal, rectal, inhalative or intravenous administration in form of e.g. tablets, gel, capsules, patches, ointments, creams. Parenteral delivery can be carried out by depot, syringe, ampoule or vial.

The compounds of the invention, together with a conventional adjuvant, carrier, or diluent, may thus be placed into the form of pharmaceutical compositions and unit dosages thereof, and in such form may be employed as solids, liquids or in the form of sterile injectable solutions. If a solid carrier is used, the preparation may be tableted, placed in a hard gelatine capsule in powder or pellet form, or in form of a troche or lozenge. The solid carrier may contain conventional excipients such as binding agents, tableting lubricants, fillers, disintegrants, wetting agents and the like. Tablets may be film coated by conventional techniques. If a liquid carrier is employed, the preparation may be in form of syrup, emulsion, soft gelatine capsule, sterile vehicle for injection, an aqueous or non-aqueous liquid suspension, or may be a dry product for reconstitution with water or other suitable vehicles before use. Liquid preparations may contain conventional additives such as suspending agents, emulsifying agents, wetting agents, non-aqueous vehicle (including edible oils), preservatives, as well as flavouring and/or colouring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Administration, however, can also be carried out rectally, e.g., in the form of suppositories, or vaginally, e.g. in the form of pessaries, tampons, creams, or percutaneously, e.g., in the form of ointments, creams or tinctures.

A suitable dose of compounds or pharmaceutical compositions according to the invention for a mammal, especially humans, suffering from, or likely to suffer from any condition as described herein is an amount of active ingredient from about 0.1 µg/kg (NB: there are few example of compounds that are delivered at lower doses, eg some hormone) to 500 mg/kg body weight. For parenteral administration, the dose may be in the range of 0.1 µg/kg to 100 mg/kg body weight for intravenous administration. The active ingredient will preferably be administered in equal doses from one to four times daily. The compounds of Formula (I) can also be used in the form of a precursor (prodrug) or a suitably modified form that releases the active compound in vivo. Normally, the administered dose will be gradually increased until the optimal effective dosage for the treated host is determined. The optimal administered dosage will be determined by a physician or others skilled in the art, depending on the relevant circumstances including the condition to be treated, the choice of compound to be administered, the route of administration, the sex, age, weight, and the specific response of the treated individual in respect to the severity of the individual's symptoms.

The pharmaceutical compositions are prepared by conventional techniques appropriate to the desired preparation containing appropriate amounts of the active ingredient, i.e., the compounds of the present invention. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The following examples further illustrate the best mode contemplated by the inventors for carrying out their invention. The examples relate to preferred embodiments and are not to be construed to be limiting on the scope of the invention.

TABLE 1

Compound activities as measured by the ELISA based protein-protein interaction assay as described in Example 1

| TGC ID | MOLSTRUCTURE | MW | PSA | ELISA | CA |
|---|---|---|---|---|---|
| TGC0012304 | | 435.3321 | 83.65 | | |
| TGC0012284 | | 523.4201 | 152.67 | | |

TABLE 1-continued

*Compound activities as measured by the ELISA based protein-protein interaction assay as described in Example 1*

| TGC ID | MOLSTRUCTURE | MW | PSA | ELISA | CA |
|---|---|---|---|---|---|
| TGC0012283 | | 430.9136 | 92.88 | | |
| TGC0012276 | | 448.9318 | 124.76 | | 4.5 |
| TGC0012273 | | 410.8824 | 124.76 | | 3.5 |
| TGC0012268 | | 371.8482 | 72.37 | | 2.5 |

TABLE 1-continued

Compound activities as measured by the ELISA based protein-protein interaction assay as described in Example 1

| TGC ID | MOLSTRUCTURE | MW | PSA | ELISA | CA |
|---|---|---|---|---|---|
| TGC0012266 | | 468.8696 | 124.43 | 2.5 | 1.5 |
| TGC0012260 | | 474.8856 | 163.35 | 4.5 | 1.5 |
| TGC0012257 | | 450.8792 | 124.43 | 1 | 1.5 |
| TGC0011601 | | 325.773 | 80.85 | 1 | 1 |

TABLE 1-continued

*Compound activities as measured by the ELISA based protein-protein interaction assay as described in Example 1*

| TGC ID | MOLSTRUCTURE | MW | PSA | ELISA | CA |
|---|---|---|---|---|---|
| TGC0011589 | | 476.8987 | 164.56 | 5 | 4 |
| TGC0011584 | | 460.9429 | 123.42 | 1 | 3 |
| TGC0011582 | | 392.8234 | 117.67 | 1 | 3 |
| TGC0011581 | | 524.9621 | 184.02 | 2 | 1 |

TABLE 1-continued

Compound activities as measured by the ELISA based protein-protein interaction assay as described in Example 1

| TGC ID | MOLSTRUCTURE | MW | PSA | ELISA | CA |
| --- | --- | --- | --- | --- | --- |
| TGC0011577 | | 561.0143 | 209.47 | 4 | 1 |
| TGC0011576 | | 517.3695 | 166.95 | 3 | 5 |
| TGC0011575 | | 539.9768 | 196.05 | 1 | 3 |

TABLE 1-continued

Compound activities as measured by the ELISA based
protein-protein interaction assay as described in Example 1

| TGC ID | MOLSTRUCTURE | MW | PSA | ELISA | CA |
|---|---|---|---|---|---|
| TGC0011574 | | 520.4386 | 96.12 | 3 | 2.5 |
| TGC0011573 | | 450.3468 | 109.67 | 3 | 1 |
| TGC0011570 | | 468.9222 | 117.67 | 5 | 4 |
| TGC0011569 | | 468.9222 | 117.67 | 1.5 | 4 |
| TGC0011568 | | 515.7623 | 141.5 | 1.5 | 4 |

TABLE 1-continued

*Compound activities as measured by the ELISA based protein-protein interaction assay as described in Example 1*

| TGC ID | MOLSTRUCTURE | MW | PSA | ELISA | CA |
|---|---|---|---|---|---|
| TGC0011564 | | 490.9258 | 143.22 | 1 | 3.5 |
| TGC0011562 | | 504.9092 | 167.8 | 2 | 1.5 |
| TGC0011514 | | 573.7998 | 128.64 | 1 | 1 |

TABLE 1-continued

Compound activities as measured by the ELISA based protein-protein interaction assay as described in Example 1

| TGC ID | MOLSTRUCTURE | MW | PSA | ELISA | CA |
|---|---|---|---|---|---|
| TGC0011513 | | 573.7998 | 128.64 | | 1 |
| TGC0011512 | | 573.7998 | 128.64 | | |
| TGC0011502 | | 403.6843 | 83.65 | 1 | 1 |
| TGC0011499 | | 404.6691 | 80.85 | 1 | 1 |
| TGC0011498 | | 495.8013 | 109.54 | 1 | 1 |

TABLE 1-continued

Compound activities as measured by the ELISA based protein-protein interaction assay as described in Example 1

| TGC ID | MOLSTRUCTURE | MW | PSA | ELISA | CA |
|---|---|---|---|---|---|
| TGC0011494 | | 404.6691 | 80.85 | 1 | 1 |
| TGC0011493 | | 536.2533 | 109.1 | 1 | 1 |
| TGC0011492 | | 371.6419 | 78.34 | 1 | 1 |
| TGC0011438 | | 543.0487 | 133.64 | 1 | 3 |

TABLE 1-continued

Compound activities as measured by the ELISA based protein-protein interaction assay as described in Example 1

| TGC ID | MOLSTRUCTURE | MW | PSA | ELISA | CA |
|---|---|---|---|---|---|
| TGC0011421 | | 509.7688 | 124.76 | 2.5 | 4 |
| TGC0011420 | | 560.0329 | 147.66 | 1 | 2 |
| TGC0011419 | | 530.0064 | 138.43 | 1.5 | 3 |
| TGC0011409 | | 507.9592 | 137.65 | 3.5 | 4.5 |

TABLE 1-continued

Compound activities as measured by the ELISA based protein-protein interaction assay as described in Example 1

| TGC ID | MOLSTRUCTURE | MW | PSA | ELISA | CA |
|---|---|---|---|---|---|
| TGC0011406 | | 523.9586 | 146.88 | | 4 |
| TGC0011405 | | 481.9209 | 137.65 | | 4.5 |
| TGC0011404 | | 530.0064 | 138.43 | 3 | 4 |

TABLE 1-continued

Compound activities as measured by the ELISA based
protein-protein interaction assay as described in Example 1

| TGC ID | MOLSTRUCTURE | MW | PSA | ELISA | CA |
|---|---|---|---|---|---|
| TGC0011403 | | 431.8604 | 137.65 | 2 | 4 |
| TGC0011402 | | 431.8604 | 137.65 | 2 | 4 |
| TGC0011401 | | 431.8604 | 137.65 | 1.5 | 4 |
| TGC0011361 | | 382.8282 | 124.76 | 1 | 3.5 |

TABLE 1-continued

Compound activities as measured by the ELISA based protein-protein interaction assay as described in Example 1

| TGC ID | MOLSTRUCTURE | MW | PSA | ELISA | CA |
|---|---|---|---|---|---|
| TGC0011360 | | 569.3808 | 183.35 | 4.5 | |
| TGC0011359 | | 446.8722 | 144.99 | 3 | 3 |
| TGC0011358 | | 487.9251 | 153.86 | 1.5 | 3 |
| TGC0011158 | | 346.632 | 54.55 | 1 | |
| TGC0011157 | | 346.632 | 54.55 | 1 | |

TABLE 1-continued

Compound activities as measured by the ELISA based
protein-protein interaction assay as described in Example 1

| TGC ID | MOLSTRUCTURE | MW | PSA | ELISA | CA |
|---|---|---|---|---|---|
| TGC0011155 | | 302.181 | 54.55 | 1 | |
| TGC0010800 | | 342.7629 | 138.42 | | |
| TGC0010719 | | 469.78 | 104.96 | | |
| TGC0010674 | | 563.3981 | 142.06 | 2.5 | |

TABLE 1-continued

Compound activities as measured by the ELISA based
protein-protein interaction assay as described in Example 1

| TGC ID | MOLSTRUCTURE | MW | PSA | ELISA | CA |
|---|---|---|---|---|---|
| TGC0010673 | | 558.4472 | 129.17 | 1 | 4.5 |
| TGC0010665 | | 499.9363 | 145.07 | 2 | 4 |
| TGC0010663 | | 471.8821 | 153.86 | 2.5 | |

TABLE 1-continued
Compound activities as measured by the ELISA based
protein-protein interaction assay as described in Example 1
| TGC ID | MOLSTRUCTURE | MW | PSA | ELISA | CA |
|---|---|---|---|---|---|
| TGC0010661 | 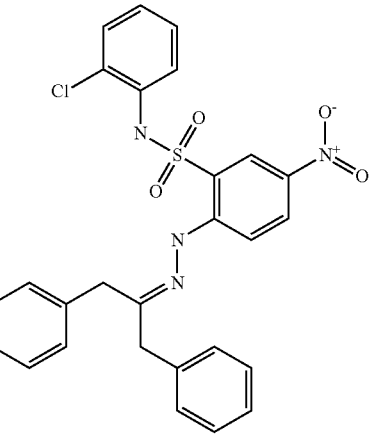 | 535.0258 | 124.76 | 2 | 3 |
| TGC0010626 | 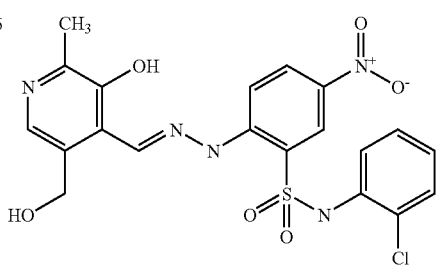 | 491.9134 | 178.11 | 3 | 4.5 |
| TGC0010583 | 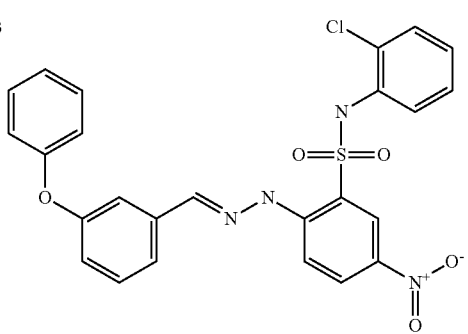 | 522.971 | 133.99 | 2 | 4 |
| TGC0010536 | 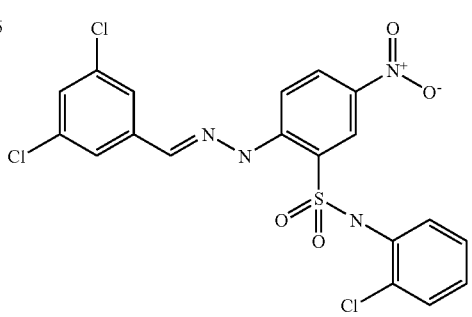 | 499.7629 | 124.76 | 2 | 5 |

TABLE 1-continued

Compound activities as measured by the ELISA based
protein-protein interaction assay as described in Example 1

| TGC ID | MOLSTRUCTURE | MW | PSA | ELISA | CA |
|---|---|---|---|---|---|
| TGC0010527 | | 515.7623 | 144.99 | 3 | 4.5 |
| TGC0008709 | | 462.8716 | 165.22 | 3.5 | 4 |

The ELISA and Cell Assay (CA) measurements were performed as described above in the examples.

The numbers referring to the ELISA and CA tests are interpreted as follows:
1: 0-20% inhibition
2: 21-40% inhibition
3: 41-60% inhibition
4: 61-80% inhibition
5: 81-100% inhibition

EXPERIMENTAL

The compounds according to the invention were prepared as follows:

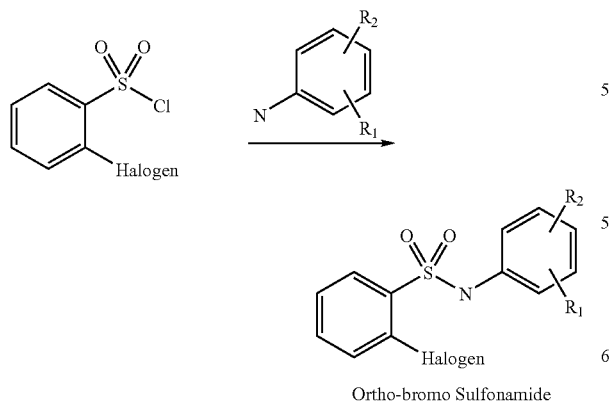

2-Bromobenzenesulfonyl chloride (1 eq) and pyridine (2 eq.) dissolved in dichloromethane (1 mL/mmol of sulfonyl chloride) were introduced in a round bottomed flask. The reaction mixture was cooled to 0° C. The substituted-aniline (1 eq.) was slowly added. The resulting mixture was allowed to stir overnight. A 0.5 M solution of hydrochloric acid was added. The organic phase was separated and washed with water then brine. The organic phase was dried over sodium sulfate, filtered and evaporated to dryness. The residue was triturated in a minimal amount of methanol. The desired compound was obtained as a white solid.

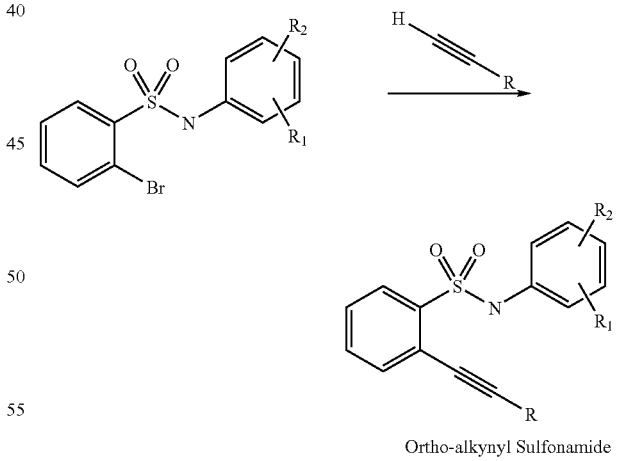

Ortho-alkynyl Sulfonamide

N-Substituted-2-Bromobenzene sulfonamide (1 eq.) was mixed with the corresponding terminal alkyne (1 eq.) in diisopropylamine (5 mL/mmol of N-substituted-2-bromobenzene sulfonamide). To this mixture, triphenylphosphine (0.01 eq), copper iodide (0.01 eq.) and acetonitrile palladium chloride complex (0.01 eq.) was added. The resulting reaction mixture was refluxed overnight, filtered through a celite bed and concentrated under reduce pressure. Column chromatography yielded the desired product as a white to yellowish powder.

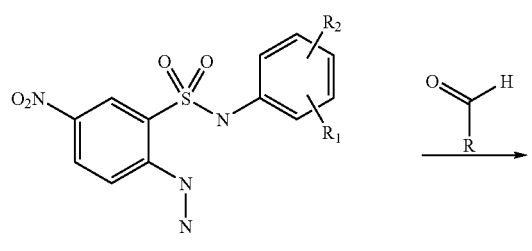

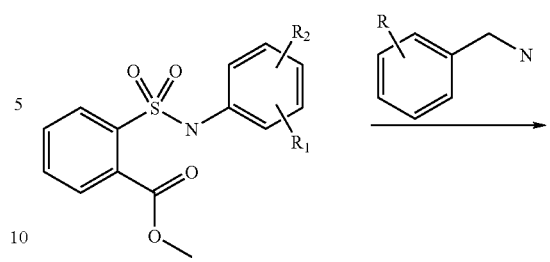

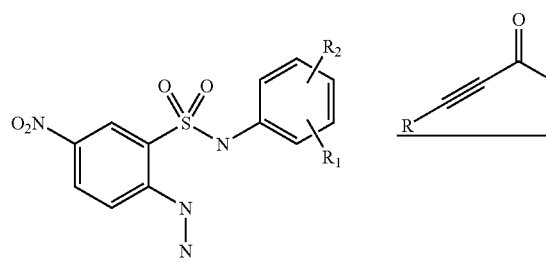

ortho-Hydrazone Sulfonamide

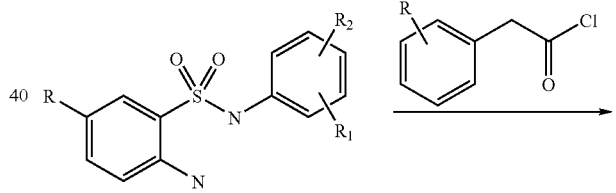

ortho-Carboxamide Sulfonamide

Sulfonamide hydrazine (1 eq.) was dissolved in THF (5 mL/mmol of hydrazine) and treated with the corresponding aldehyde (1 eq.) in the presence of a catalytic amount of p-toluene sulfonic acid at reflux temperature overnight. The resulting reaction mixture was concentrated under reduced pressure and the residue recrystallized from methanol and/or column chromatographed to yield the desired product as a bright yellowish powder.

ortho-Methylcarboxylate sulfonamide (1 eq) was mixed with the corresponding benzylamine (1 eq.) in acetonitrile (5 mL/mmol of ester). The reaction mixture was heated to 50° C. for half hour and triethylamine (1.2 eq.) neat was added. The resulting mixture was allowed to reflux overnight. Upon evaporation of the solvent, column chromatography yields the desired carboxamide sulfonamide as a white solid.

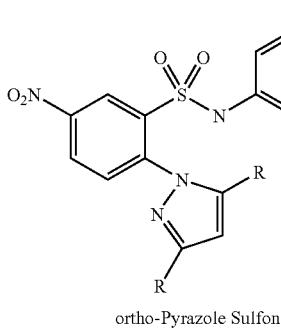

ortho-Pyrazole Sulfonamide ortho-Amide Sulfonamide

Sulfonamide hydrazine (1 eq.) was dissolved in absolute ethanol (5 mL/mmol of hydrazine) and treated with the corresponding ketoalkyne (1 eq.) at reflux temperature for 4 h. The resulting reaction mixture was concentrated under reduced pressure and the residue recrystallized from methanol and/or column chromatographed to yield the desired product as a bright yellowish powder.

The substituted acyl chloride (1 eq.) was dissolved in dichloromethane (5 mL/mmol of acyl chloride) and cooled to 0° C. Cold pyridine (2 eq.) dissolved in dichloromethane (5 mL/mmol acyl chloride) was slowly added and the resulting solution allowed to warm up to room temperature over a 2 h period. The resulting reaction mixture was cooled to 0° C. A solution of 2-Amino-4-substituted benzenesulfonyl amide (1 eq) in dichloromethane (5 mL/mmol of sulfonyl amide) was slowly syringed in. The reaction mixture was allowed to stir overnight while the temperature warmed up to room temperature. A 0.5 M solution of hydrochloric acid was added. The organic phase is separated and washed with water then brine. The organic phase was dried over sodium sulfate, filtered and evaporated to dryness. The residue is triturated in a minimal amount of methanol and column chromatographed obtaining the desired product as a white solid.

Selected Mass Spectral and 1H-NMR data. (signals given in ppm in reference to deuterated dimethylsulfoxide, s: singlet, d: doblet, t: triplet, q: quartet, dd: doblet of doblets, dt: doblet of triplets, m: multiplet and b: broad band).

| TGC ID | MOLSTRUCTURE | MS | 1H—NMR |
|---|---|---|---|
| TGC0012304 | 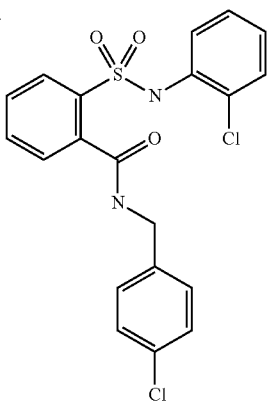 | 434 | 4.67 (d, 2H), 7.03 (t, 1H), 7.24-7.19 (m, 3H), 7.37-7.34 (m, 3H), 7.74-7.52 (m, 4H), 7.75 (d, 1H), 8.68 (bs, 1H). |
| TGC0012284 | 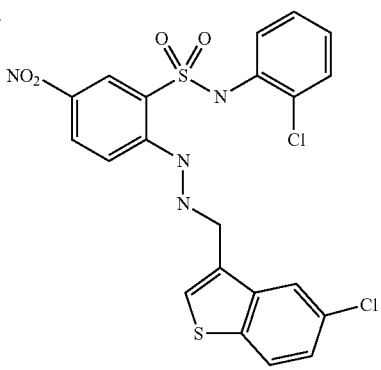 | 521 | 5.00 (dd, 2H), 7.73-7.14 (m, 12H), 8.52 (d, 1H), 8.53 (s, 1H). |
| TGC0012283 | 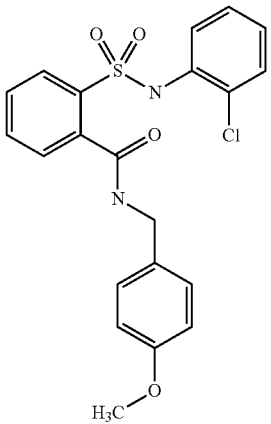 | 430 | 3.81 (s, 3H), 6.24 (t, 1H), 7.00 (q, 2H), 7.06 (t, 1H), 7.27-7.22 (m, 2H), 7.36 (d, 2H), 7.55 (m, 1H), 7.56 (m, 2H), 7.63 (d, 1H), 7.78 (d, 1H), 8.80 (s, 1H). |

-continued

| TGC ID | MOLSTRUCTURE | MS | 1H—NMR |
|---|---|---|---|
| TGC0012276 | | 448 | 0.89 (t, 3H), 1.40-1.28 (m, 4H), 1.59 (quintet, 2H), 2.57-2.48 (m, 2H), 6.81 (s, 1H), 7.35-7.25 (m, 3H), 7.43 (dt, 1H), 7.62 (d, 1H), 8.33 (dd, 1H), 8.41 (d, 1H), 10.59 (s, 1H), 10.62 (s, 1H). |
| TGC0012273 | | 410 | 0.94 (s, 3H), 0.96 (s, 3H), 1.90 (septuplet, 1H), 2.21 (t, 2H), 7.22 (dt, 1H), 7.33 (dt, 1H), 7.40 (dd, 2H), 7.60 (t, 1H), 7.62 (d, 1H), 8.21 (d, 1H), 8.25 (dd, 1H), 9.83 (s, 1H), 10.49 (s, 1H). |
| GC0012266 | | N.A. | 2.40-1.70 (b, 2H), 4.72 (q, 2H), 6.72-6.63 (m, 3H), 7.21-7.13 (m, 4H), 7.29 (d, 1H), 7.46 (d, 1H), 7.63 (s, 1H), 8.18 (d, 1H), 8.42 (s, 1H). |
| TGC0012260 | | 474 | 3.57 (bs, 2H), 4.92 (q, 2H), 7.27-7.19 (m, 3H), 7.60-7.50 (m, 4H), 7.82 (s, 1H), 7.84 (d, 1H), 8.25 (d, 1H), 8.54 (s, 1H). |

| TGC ID | MOLSTRUCTURE | MS | 1H—NMR |
|---|---|---|---|
| TGC0012257 | 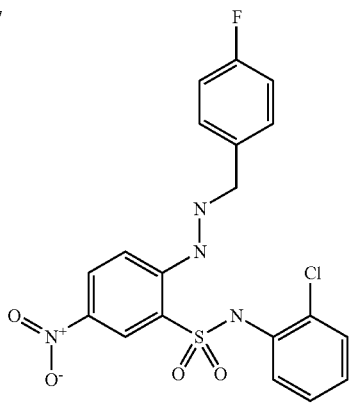 | 451 | 3.53 (bs, 2H), 4.83 (q, 2H), 6.92 (t, 3H), 7.18-7.13 (m, 5H), 7.22 (d, 1H), 7.69 (s, 1H), 8.32 (d, 1H), 8.53 (s, 1H). |
| TGC0011589 | 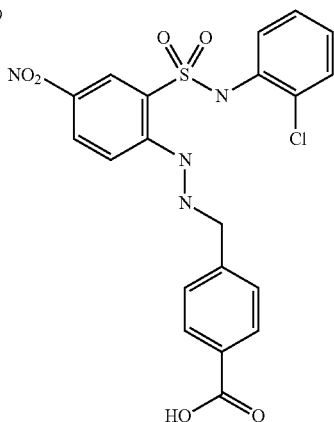 | 475 | 4.65 (bt, 2H), 6.47 (t, 1H), 6.85 (t, 1H), 7.23-7.02 (m, 5H), 7.74-7.32 (m, 2H), 7.22 (d, 1H), 8.25 (d, 1H), 8.65 (d, 1H), 8.98 (s, 1H), 10.55 (s, 1H). |
| TGC0011582 | 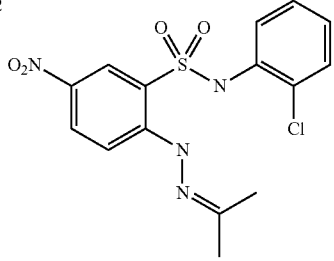 | 382 | 1.79 (s, 3H), 2.02 (s, 3H), 7.37-7.25 (m, 3H), 7.43 (d, 1H), 7.59 (d, 1H), 8.22 (d, 1H), 8.28 (dd, 1H), 9.48 (s, 1H), 10.62 (s, 1H). |
| TGC0011574 | 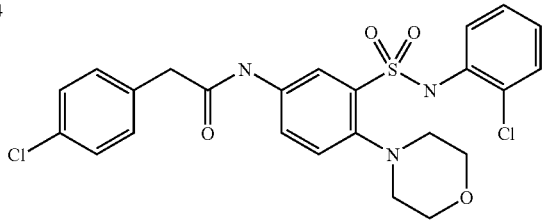 | N.A. | 2.97 (t, 4H), 3.66 (s, 2H), 3.88 (t, 4H), 6.93 (t, 1H), 7.09 (t, 1H), 7.23-7.21 (m, 5H), 7.32 (t, 2H), 7.48 (d, 1H), 7.69 (d, 1H), 8.05 (d, 1H), 8.07 (s, 1H). |

-continued
| TGC ID | MOLSTRUCTURE | MS | 1H—NMR |
|---|---|---|---|
| TGC0011573 | 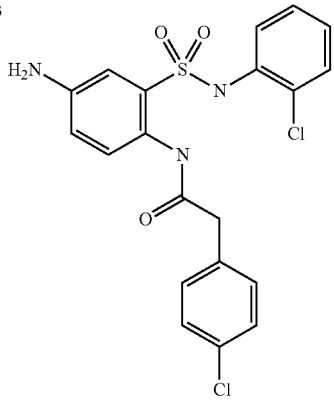 | 450 | 3.69 (bs, 2H), 5.83 (bs, 2H), 6.73 (d, 1H), 7.26-7.13 (bm, 4H), 7.40 (bd, 5H), 7.66 (bs, 1H), 9.40 (bs, 1H), 9.64 (bd, 1H). |
| TGC0011570 | 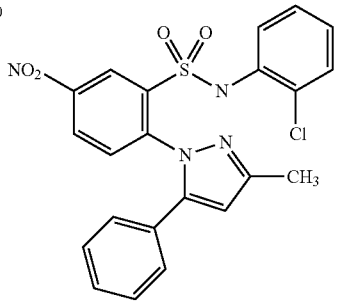 | 469 | 2.22 (s, 3H), 7.29-7.13 (m, 3H), 7.36 (dd, 1H), 7.57-7.51 (m, 3H), 7.66 (d, 1H), 7.76-7.70 (m, 2H), 8.37-8.31 (m, 2H), 10.58 (s, 1H), 10.68 (s, 1H). |
| TGC0011564 | 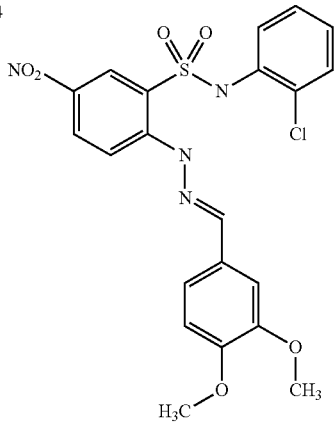 | 491 | 3.80 (s, 3H), 3.84 (s, 3H), 7.03 (d, 2H), 7.37-7.21 (m, 6H), 7.87 (d, 1H), 8.25-8.20 (m, 2H), 8.27 (d, 1H), 10.10 (s, 1H), 10.70-10.60 (b, 1H). |
| TGC0011419 | 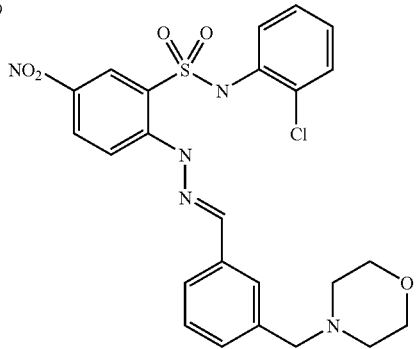 | 530 | 3.33-3.12 (m, 4H), 3.66 (t, 2H), 3.97 (d, 2H), 4.45 (d, 2H), 7.23 (t, 1H), 7.42-7.30 (m, 3H), 7.58 (d, 2H), 7.83 (d, 1H), 7.92 (d, 1H), 8.01 (s, 1H), 8.23 (d, 1H), 8.33 (s, 2H), 10.28 (s, 1H), 10.57 (b, 1H). |

| TGC ID | MOLSTRUCTURE | MS | 1H—NMR |
|---|---|---|---|
| TGC0011406 | | N.A. | 7.04 (d, 2H), 7.19, 7.15 (m, 2H), 7.42-7.33 (m, 7H), 7.45 (t, 2H), 7.83 (d, 1H), 8.22 (s,1H), 8.28 (bs, 2H), 10.20 (s, 1H), 10.54 (bs, 1H). |
| TGC0011405 | | N.A. | 7.36 (t, 1H), 7.43-7.39 (m, 3H), 7.98 (t, 1H), 8.04 (t, 2H), 8.22 (d, 1H), 8.31 (t, 2H), 8.42 (d, 1H), 8.73 (d, 1H), 9.18 (d, 2H), 10.72 (bs, 2H). |
| TGC0011361 | | 383 | 1.10 (t, 3H), 2.35 (dt, 2H), 7.25 (dt, 1H), 7.48-7.36 (m, 3H), 7.66-7.58 (m, 2H), 8.22 (d, 1H), 8.26 (dd, 1H), 9.80 (s, 1H), 10.45 (s, 1H). |
| TGC0011359 | | 447 | 6.85 (d, 2H), 7.22-7.18 (m, 1H), 7.38 (t, 3H), 7.64 (d, 2H), 7.81 (d, 1H), 8.22 (t, 2H), 8.28 (d, 1H), 10.02 (s, 1H), 10.06 (s, 1H), 10.53 (s, 1H). |

-continued

| TGC ID | MOLSTRUCTURE | MS | 1H—NMR |
|---|---|---|---|
| TGC0011358 | | 488 | 2.07 (s, 3H), 7.22 (t, 1H), 7.38 (t, 3H), 7.71 (q, 4H), 7.84 (d, 1H), 8.22 (s, 2H), 8.32 (d, 1H), 10.16 (d, 2H), 10.55 (bs, 1H). |
| TGC0010536 | | 501 | 7.23 (dt, 1H), 7.38 (dt, 3H), 7.68 (t, 1H), 7.86 (d, 2H), 8.00 (d, 1H), 8.23 (dd, 2H), 8.30 (dd, 1H), 10.35 (s, 1H), 10.60 (bs, 1H). |
| TGC0010527 | | 516 | 7.20 (t, 1H), 7.41-7.33 (m, 3H), 7.61 (d, 1H), 7.82 (s, 1H), 7.89 (d, 1H), 8.20 (s, 1H), 8.32 (d, 1H), 8.60 (s, 1H), 10.38 (bs, 1H), 10.51 (s, 1H), 10.54 (bs, 1H). |
| TGC0008709 | | 463 | 6.80 (d, 1H), 7.04 (dd, 2H), 7.25 (d, 2H), 7.36 (t, 2H), 7.69 (d, 1H), 8.09 (s, 1H), 8.26 (s, 2H), 9.26 (s, 1H), 9.50 (s, 1H), 10.33 (bs, 1H), 10.51 (bs, 1H). |

EXAMPLES

Example 1

In vitro ELISA-based Protein-protein Interaction Assay

Protein Production in Bacteria cDNAs including the binding domains of Lgs and βCatenin were fused downstream of glutathione-S-transferase (GST) cDNA in pGEX-4T inducible bacterial expression vector (Pharmacia). Fusion proteins were produced in BL21 bacteria (e.g. Stratagene) following manufacturer's recommendation.

To isolate the produced fusions protein bacteria were lysed in sonication buffer (10 mM Tris HCl pH 8.0, 150 mM NaCl, 1 mM EDTA, 1.5% sarkosyl, 2% Triton-X-100, 1 mM DTT and protease inhibitors), followed by short sonication on ice (e.g. 3 times 20 seconds at middle power) and centrifugation. Cleared supernatants were incubated under gentle rotation with glutathione beads (Amersham Pharmacia) for 2 hrs at 4° C. Finally, beads were washed several time in washing buffer (20 mM Tris pH 8.0, 200 mM NaCl, 1 mM EDTA, 1 mM DTT, 1 mM MgCl₂, 0.5% NP40), and stored in storage buffer (20 mM Tris pH 8.0, 200 mM NaCl, 1 mM EDTA, 1 mM DTT, 1 mM MgCl2, 10% glycerol, 0.5% NP40, and proteinase inhibitors). The quality of the preparations was checked by SDS-gel electrophoresis by standard methods well known by persons skilled in the art.

Binding Assay

To test binding of the mutants to the corresponding partner, glutathione S-transferase (GST) fusion proteins immobilized on glutathione beads as described above were blocked in binding buffer (20 mM Tris pH 8.0, 200 mM NaCl, 1 mM EDTA, 1 mM DTT, 1 mM MgCl2, 10% glycerol, 0.5% NP40, 0.05% BSA, and proteinase inhibitors) for 45 min. Two μg of immobilized GST proteins were then incubated for 1.5 hrs with 0.5-4 μl of IVT proteins in binding buffer. Beads were then washed four times in washing buffer (20 mM Tris pH 8.0, 200 mM NaCl, 1 mM EDTA, 1 mM DTT, 1 mM MgCl$_2$, 0.5% NP40) and boiled in Laemmli SDS sample buffer. The use of equivalent amounts of intact GST-fusions and IVT proteins was confirmed by SDS-PAGE analysis using Coomassie staining and autoradiography, respectively.

Example 2

Inhibition of Wnt Activity in Cancer Cells

The effect of β-catenin/BCL9 inhibitors identified in the ELISA-based protein-protein interaction assay on the Wnt pathway can be evaluated in a cell culture system using a reporter gene responsive to the Tcf/Lef family of transcription factors or by quantitative analysis of Wnt target genes in appropriate cell lines.

A reporter gene is a construct which comprises a readily detectable or assayable gene such β-galactosidase, green fluorescent protein, chloramphenicol acetyltransferase or luciferase, linked in cis to a transcription factor response element and a minimal promoter. Depending on the expression vectors used, this protocol can be applied, e.g. for mammalian as well as for *Drosophila* cell lines. For instance, colon cancer cells with constitutively active Wnt pathway like DLD-1 or SW620 (ATCC) are a well suitable system. Hereby, a Tcf-4 driven luciferase reporter plasmid (i.e. TOP-FLASH, Upstate biotechnology, New York, USA) is transiently or stably transfected into cells known in the art. Any means for introducing genetic material into cells can be used, including but not limited to infection, electroporation or transfection. For instance, to introduce DNA into DLD-1 cells, a lipofection agent like the Lipofectamine transfection reagent (Life Technologies, Inc.) can be used. By transient transfection protocols, a second reporter gene, e.g. the renilla luciferase reporter plasmid pRL-SV40 (Promega Corporation, Madison USA), needs to be co-transfected to normalize for transfection efficiency. Drugs are added to the media 24 h after transfection (transient transfection) or 24 h after seeding of the cells (stably transfected cells). Cell extracts are prepared 24 to 48 h later and assayed for reporter gene activity as described by the manufacturer (eg. for luciferase activity: Promega Corporation). Compounds reducing reporter gene activity more than 50% compared to solvent alone treated cells are considered as hits. In parallel, toxicity can be assessed for instance by the yellow tetrazolium salt cell proliferation assay (MTT) assay.

REFERENCES

Bartel, P. L. and S. Fields (1995). "Analyzing protein-protein interactions using two-hybrid system." *Methods Enzymol* 254: 241-63.

Boute, N., R. Jockers, et al. (2002). "The use of resonance energy transfer in high-throughput screening: BRET versus FRET." *Trends Pharmacol Sci* 23(8): 351-4.

Caca, K., F. T. Kolligs, et al. (1999). "Beta- and gamma-catenin mutations, but not E-cadherin inactivation, underlie T-cell factor/lymphoid enhancer factor transcriptional deregulation in gastric and pancreatic cancer." *Cell Growth Differ* 10(6): 369-76.

Crawford, H. C., B. M. Fingleton, et al. (1999). "The metalloproteinase matrilysin is, a target of beta-catenin transactivation in intestinal tumors." *Oncogene* 18(18): 2883-91.

Eklof Spink, K., S. G. Fridman, et al. (2001). "Molecular mechanisms of beta-catenin recognition by adenomatous polyposis coli revealed by the structure of an APC-beta-catenin complex." *Embo J* 20(22): 6203-12.

Gonzalez, J. E. and P. A. Negulescu (1998). "Intracellular detection assays for high-throughput screening." *Curr Opin Biotechnol* 9(6): 624-31.

Graham, T. A., C. Weaver, et al. (2000). "Crystal structure of a beta-catenin/Tcf complex." *Cell* 103(6): 885-96.

He, T. C., A. B. Sparks, et al. (1998). "Identification of c-MYC as a target of the APC pathway [see comments]." *Science* 281(5382): 1509-12.

Huber, A. H. and W. I. Weis (2001). "The structure of the beta-catenin/E-cadherin complex and the molecular basis of diverse ligand recognition by beta-catenin." *Cell* 105(3): 391-402.

Kinzler, K. W. and B. Vogelstein (1996). "Lessons from hereditary colorectal cancer." *Cell* 87(2): 159-70.

Kolligs, F. T., M. T. Nieman, et al. (2002). "ITF-2, a downstream target of the Wnt/TCF pathway, is activated in human cancers with beta-catenin defects and promotes neoplastic transformation." *Cancer Cell* 1(2): 145-55.

Kramps, T., O. Peter, et al. (2002). "Wnt/wingless signaling requires BCL9/legless-mediated recruitment of pygopus to the nuclear beta-catenin-TCF complex." *Cell* 109(1): 47-60.

Miller, J. R., A. M. Hocking, et al. (1999). "Mechanism and function of signal transduction by the Wnt/beta-catenin and Wnt/Ca2+ pathways." *Oncogene* 18(55): 7860-72.

Morin, P. J., A. B. Sparks, et al. (1997). "Activation of beta-catenin-Tcf signaling in colon cancer by mutations in beta-catenin or APC [see comments]." *Science* 275(5307): 1787-90.

Nasir, M. S, and M. E. Jolley (1999). "Fluorescence polarization: an analytical tool for immunoassay and drug discovery." *Comb Chem High Throughput Screen* 2(4): 177-90.

Poy, F., M. Lepourcelet, et al. (2001). "Structure of a human Tcf-4-beta-catenin complex." *Nat Struct Biol* 8(12): 1053-7.

Rubinfeld, B., P. Robbins, et al. (1997). "Stabilization of beta-catenin by genetic defects in melanoma cell lines." *Science* 275(5307): 1790-2.

Satoh, S., Y. Daigo, et al. (2000). "AXIN1 mutations in hepatocellular carcinomas, and growth suppression in cancer cells by virus-mediated transfer of AXIN1." *Nat Genet.* 24(3): 245-50.

Shtutman, M., J. Zhurinsky, et al. (2002). "PML is a target gene of beta-catenin and plakoglobin, and coactivates beta-catenin-mediated transcription." *Cancer Res* 62(20): 5947-54.

Staal, F. J. and H. C. Clevers (2003). "Wnt signaling in the thymus." *Curr Opin Immunol* 15(2): 204-8.

Staal, F. J., J. Meeldijk, et al. (2001). "Wnt signaling is required for thymocyte development and activates Tcf-1 mediated transcription." *Eur J Immunol* 31(1): 285-93.

Tetsu, O. and F. McCormick (1999). "Beta-catenin regulates expression of cyclin D1 in colon carcinoma cells." *Nature* 398(6726): 422-6.

Topcu, Z. and K. L. Borden (2000). "The yeast two-hybrid system and its pharmaceutical significance." *Pharm Res* 17(9): 1049-55.

van de Wetering, M., R. Cavallo, et al. (1997). "Armadillo coactivates transcription driven by the product of the *Drosophila* segment polarity gene dTCF." *Cell* 88(6): 789-99.

The invention claimed is:

1. A sulfonamide compound of formula I:

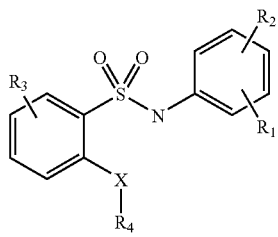

wherein
R1 is selected from the group consisting of H, CN, halogen, trifluoromethyl, methyl, ethyl, hydroxy, methoxy, ethoxy, morpholino,
$R_2$ is selected from the group consisting of H, phenyl, substituted phenyl, CN, and —$SO_2R$, wherein R is phenyl or morpholino, —NC(O)Me, —NC(O)Et, —$CH_2C(O)OMe$, or $CH_2C(O)OEt$,
$R_3$ is selected from the group consisting of, $NO_2$, $NH_2$, halogen, —COOMe, —COOEt, and morpholino,
$R_4$ is selected from the group consisting of a branched or unbranched methyl, ethyl, propyl, butyl, pentyl, methoxy, ethoxy, propoxy, butoxy, a substituted or unsubstituted phenyl, alkenyl, $Me_2SO_2$—, and COOR, wherein R is a branched or unbranched methyl, ethyl, propyl, butyl, pentyl, -MeOC(O)—, or a substituted or unsubstituted pyrazolyl or pyridinyl,
X is a linker selected from the group consisting of —NH—NH—, —NH—NH—$CH_2$—, ethinyl, —NH—C(O)—$CH_2$—, —NH—NH—$SO_2$—, —C(O)—NH—$CH_2$—, —NH—N=CH—, —NH—N=C(Me)-, and a substituted or unsubstituted pyrazole or pyridazine,
or a pharmaceutically acceptable salt thereof.

2. The sulphonamide compound according to claim 1, wherein $R_1$ is located in ortho position.

3. The sulphonamide compound according to claim 2, wherein $R_1$ is a halogen.

4. The sulphonamide compound according to claim 1, wherein $R_2$ is located in meta position.

5. The sulphonamide compound according to claim 1, wherein $R_2$ is located in para position.

6. The sulphonamide compound according to claim 1, wherein $R_3$ is located in ortho position.

7. The sulphonamide compound according to claim 6, wherein $R_3$ is halogen.

8. The sulphonamide compound according to claim 1, wherein $R_3$ is located in meta position.

9. The sulphonamide compound according to claim 8, wherein $R_3$ is $H$, halogen, $NO_2$, or $NH_2$.

10. The sulphonamide compound according to claim 9, wherein $R_3$ is in para position to the X—$R_4$ group.

11. A sulphonamide compound according to claim 10, wherein X is selected from the group consisting of —NH—NH—, —NH—NH—$CH_2$—, ethinyl, —NH—C(O)—$CH_2$—, —NH—NH—$SO_2$—, —C(O)—NH—$CH_2$—, —NH—N=CH—, —NH—N=C(Me)-, and a substituted or unsubstituted pyrazole.

12. The sulphonamide compound according to claim 11, wherein $R_4$ is selected from the group consisting of a branched or unbranched methyl, ethyl, propyl, butyl, pentyl, methoxy, ethoxy, a substituted or unsubstituted phenyl, a substituted alkinyl, $Me_2SO2$-, and COOR, wherein R is a branched or unbranched methyl, ethyl, propyl, butyl, pentyl, -MeOC(O)—, or a substituted or unsubstituted pyrazolyl or pyridinyl.

13. The sulphonamide compound according to claim 12, wherein $R_3$ is $NO_2$.

14. A sulphonamide compound according to claim 1, wherein X is selected from the group consisting of —$NH_2$—NH—$CH_2$—, —$NH_2$—$NH_2$—$SO_2$—, —NH=N—$CH_2$—, a substituted or unsubstituted pyrazole, and —$NH_2$—NH—C(O)—.

15. The sulphonamide compound according to claim 14 with the following formula II:

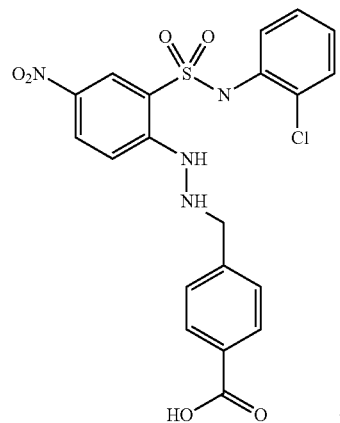

16. The sulphonamide compound according to claim 14 with the following formula III:

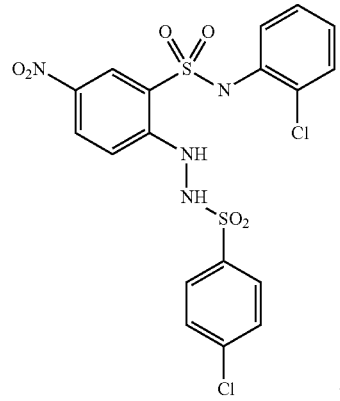

17. The sulphonamide compound according to claim 14 with the following formula IV:

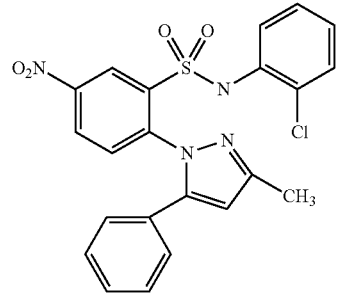

18. The sulphonamide compound according to claim 14 with the following formula V:

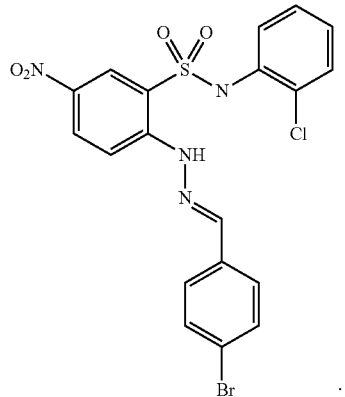

19. The sulphonamide compound according to claim 14 with the following formula VI:

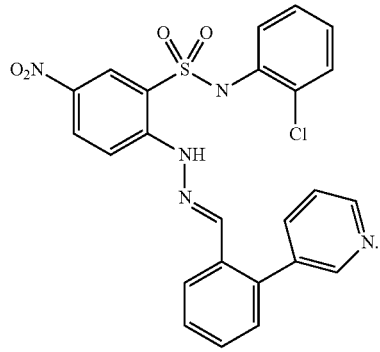

20. The sulphonamide compound according to claim 14 with the following formula VII:

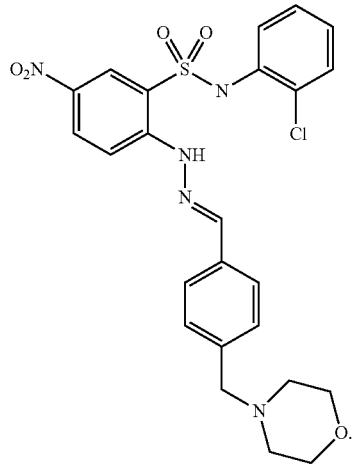

21. The sulphonamide compound according to claim 14 with the following formula VIII:

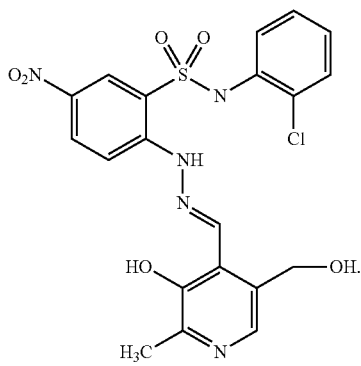

22. The sulphonamide compound according to claim 14 with the following formula IX:

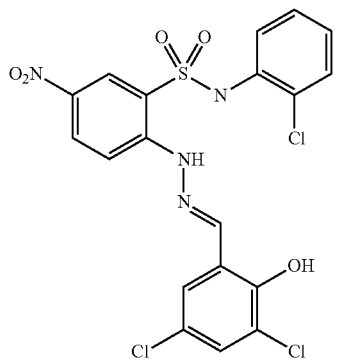

23. A pharmaceutical composition comprising the compound according to claim 1 or a pharmaceutically acceptable salt thereof.

24. The pharmaceutical composition according to claim 23, further comprising at least one pharmaceutically acceptable carrier, diluent or excipient.

* * * * *